(12) United States Patent
Prause

(10) Patent No.: US 6,739,188 B1
(45) Date of Patent: May 25, 2004

(54) TESTING DEVICE FOR THE ULTRASONIC INSPECTION OF BARSTOCK

(75) Inventor: Reinhard Prause, St. Augustin (DE)

(73) Assignee: Agfa NDT GmbH (DE)

( * ) Notice: Subject to any disclaimer, the term of this patent is extended or adjusted under 35 U.S.C. 154(b) by 36 days.

(21) Appl. No.: 10/415,067

(22) PCT Filed: Oct. 24, 2000

(86) PCT No.: PCT/DE00/03747

§ 371 (c)(1),
(2), (4) Date: Apr. 24, 2003

(87) PCT Pub. No.: WO02/35226

PCT Pub. Date: May 2, 2002

(51) Int. Cl.[7] .................................................. G01F 3/56
(52) U.S. Cl. .......................... 73/305; 73/54.11; 73/290; 73/600
(58) Field of Search ........................ 73/305, 290, 54.11, 73/600, 625, 660, 661

(56) References Cited

U.S. PATENT DOCUMENTS

| 3,413,843 A | | 12/1968 | Kortenhoven et al. | ........ 73/600 |
| 3,850,027 A | * | 11/1974 | Nakanishi et al. | ............ 73/600 |
| 3,911,750 A | * | 10/1975 | Prasher | ...................... 73/866.5 |
| 4,305,297 A | * | 12/1981 | Ries et al. | ..................... 73/628 |
| 4,594,897 A | * | 6/1986 | Bantz | ........................... 73/600 |
| 5,335,546 A | * | 8/1994 | Karbach et al. | ............... 73/622 |
| 5,359,895 A | * | 11/1994 | Isenberg et al. | .............. 73/582 |

FOREIGN PATENT DOCUMENTS

| JP | 61-260160 A | 11/1986 |
| JP | 09-304358 A | 11/1997 |

* cited by examiner

*Primary Examiner*—Hezron Williams
*Assistant Examiner*—Jacques Saint-Surin
(74) *Attorney, Agent, or Firm*—Akerman Senterfitt

(57) ABSTRACT

The invention relates to a test device for the ultrasonic testing of strand material, comprising a) a stationary container that defines a substantially cylindrical interior space that has a larger diameter than the strand material and that has a cylinder axis, and b) a device for producing a peripheral water jacket that is associated either with at least one nozzle for a water feed disposed substantially tangential to an inner surface of the interior space and leading to said interior space, and/or with a bucket wheel that rotates about the cylinder axis and that is provided with a drive unit, and c) at least one ultrasonic probe that is linked with the container and that has an active surface that is freely accessible from the cylindrical interior space.

10 Claims, 2 Drawing Sheets

TESTING DEVICE FOR THE ULTRASONIC INSPECTION OF BARSTOCK

Figure 1:
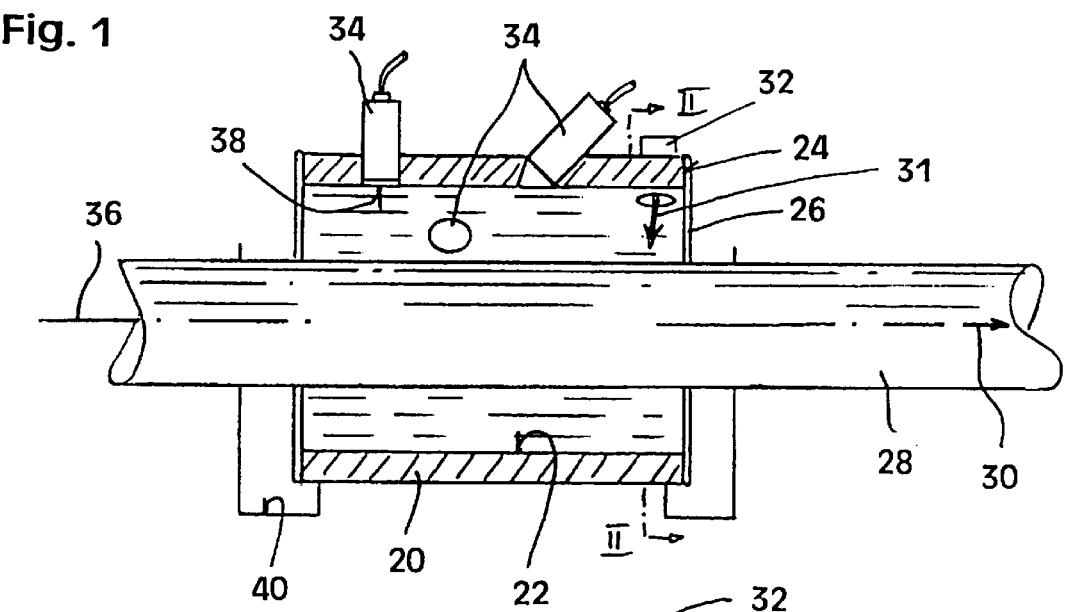

The invention relates to a testing device for the ultrasonic inspection of barstock. Such type testing devices are known in a variety of realizations; by way of example the reader is referred to the DE-book "Werkstoffprüfung mit Ultraschall" ("Material Inspection with Ultrasounds"), 4th edition, by the authors J. Krautkrämer & H. Krautkrämer.

The inspection of barstock more specifically involves detection of internal flaws and of surface flaws but also comprises the testing of the dimensions. It is known that for ultrasonic inspection a water path is to be provided and maintained between the ultrasonic probe and the bar to be tested. Several techniques are known to achieve this such as e.g., immersion testing, partial immersion testing or inspection by means of a guided water jet. Further, closed water tanks exist, which are often termed SPS and through which the test samples are conveyed. After the test sample has entered the closed water tank, the test sample seals the tank inlet and outlet. The water tank is filled with water in order to achieve the coupling between the probe and the test sample. The probes may thereby be disposed in a circumferential symmetry. The disadvantage thereof is the quite long time needed for the tank to be filled with water, end portions remaining untreated. Further, air bubbles in the coupling water compromise the inspection.

Rotary testing devices are moreover known. Rotation of the entire testing chamber together with the probes permits to generate a stable water jacket. Through sealing systems disposed on the inlet and on the outlet side a substantially tubular water jacket through which the test samples can be conveyed is obtained. This type of testing technique has a high testing efficiency but also involves high mechanical expense because of the rotating testing chamber. The term "barstock" is to be construed herein after as any kind of elongated material, more specifically round steel bars, bars with non round profiles such as square and hexagonal bars, flat material in the form of rods, but also tubes and rolling stock, extruded profiles.

It is the object of the invention to indicate a device for the ultrasonic inspection of barstock that has the advantages of the above mentioned rotary testing device but which is mechanically simple in construction, which requires little preparation prior to ultrasonic inspection and in which the probes can be disposed anywhere on the circumference.

This objective is accomplished by a testing device for the ultrasonic inspection of barstock a) with a stationary tank defining a substantially cylindrical interior space that has a larger diameter than the barstock and is provided with a cylinder's axis, b) with an equipment for producing a surrounding water jacket, said equipment being provided with either at least one nozzle for a water supply which is disposed in substantially tangential contact with an inner lining of the interior space into which it discharges and/or a blade wheel that is disposed so as to rotate about the cylinder's axis and that is assigned a rotary drive mechanism and c) with at least one ultrasonic probe that is connected to the tank and has an active face which is freely accessible from the cylindrical interior space.

Water is introduced through the nozzle which is in tangential contact and discharges into the interior space of the tank. Through this supply line and the resulting rotational movement of the water a substantially tubular water jacket is obtained. Unwanted air bubbles do not remain stationary but are swept along and are therefore insignificant in testing. The tank does not rotate, it rather remains stationary. What rotates though is the water jacket within the tank. As the water jacket rotates it is stable so that testing may be carried out immediately after a test sample in the form of a bar has entered. The rotating water jacket may be as well produced by the blade wheel. The term "blade wheel" is to be construed as any arrangement of blades, which are oriented in a more or less radial direction, that is capable of moving the water within the tank in such a manner that the revolving water jacket is obtained. The blade wheel is preferably disposed on front faces. It may be substituted for the front faces. The blade wheels are preferably positioned outside the ultrasound path of the at least one ultrasonic probe. It is also possible though that the ultrasonic probes emit sound energy through the range of movement of the blades of a blade wheel. In this case, they are matched to the movement of the blade wheel in such a manner that a measurement only occurs when there is no blade wheel in the ultrasound path.

The tank may have a very short structure. Untested end portions remain small. It is however also possible to perform the final testing inside the tank if there is an end region of a bar to be tested in the interior space.

At least one ultrasonic probe is disposed on the tank, a great multitude of probes is preferably provided for. They can be disposed anywhere on the circumference. Probe clusters or probe arrays can also be utilized. Accordingly, they can be oriented radially or inclined at any angle within the possible ultrasonic emission angles, e.g., inclined in the radial plane or at an angle different from 90 degrees to the cylinder's axis.

The ultrasonic probes have an active face that is preferably formed by a leading body made from an appropriate solid material. Said leading body may be formed in such a manner that it is made flush with the tank, i.e., that it does not impair the rotation of the water within the tubular tank.

The parts to be tested are conveyed through the interior space in a direction that is substantially concentric with the cylinder's axis. It is however also possible to inspect stationary bars or profiles by having the tank made from two shells that are to be joined together in an axial plane, are placed around a stationary bar, a tube for example, and can be axially displaced in order to perform the inspection.

Guide means for the barstock are provided on the two front faces of the tubular tank and are devised for guiding the bar to be tested so that the bar to be tested is positioned in such a manner that it is substantially concentric with the cylinder's axis. Suited sealing means are preferably provided for keeping the exit of water in the region of the front faces low. It is however also possible to deliberately have the water exiting in the region of the front faces so that the seals can be very simple or even dispensed with on the one side and that no separate outlet is required on the other side. A separate outlet may be provided for though, said outlet being configured according to the at least one nozzle for water supply and allowing the water to exit tangentially in the direction of rotation.

For sealing the region of the front faces, replaceable end rings that can be readily removably fastened to the two front faces of the tank have proved particularly efficient. They exist in various realizations, i.e., with differing central openings that are adapted to the respective one of the barstock to be tested, namely to the profile thereof.

In the region of the front faces, at the site where the end rings are disposed, water may, possibly is even intended to, exit. Collecting basins for collecting the exiting water are therefore disposed beneath the front faces.

Figure 2:
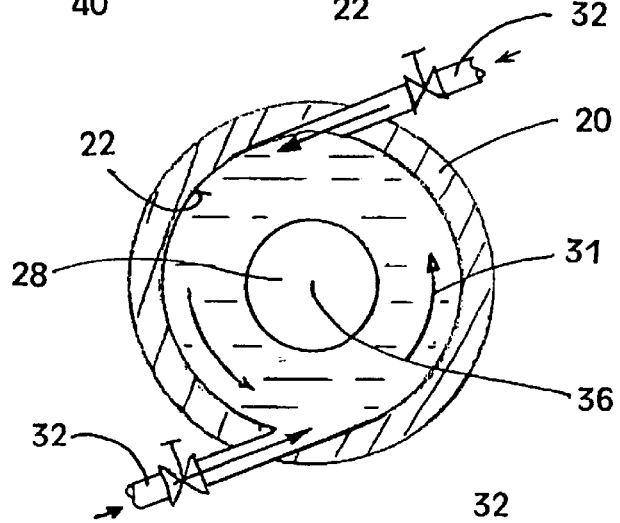
Figure 3:
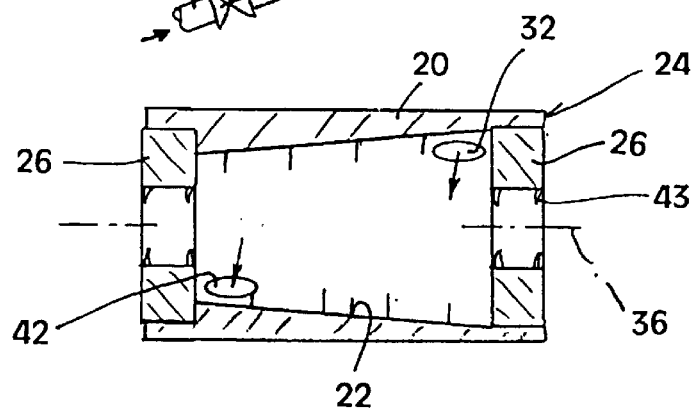
Figure 6:
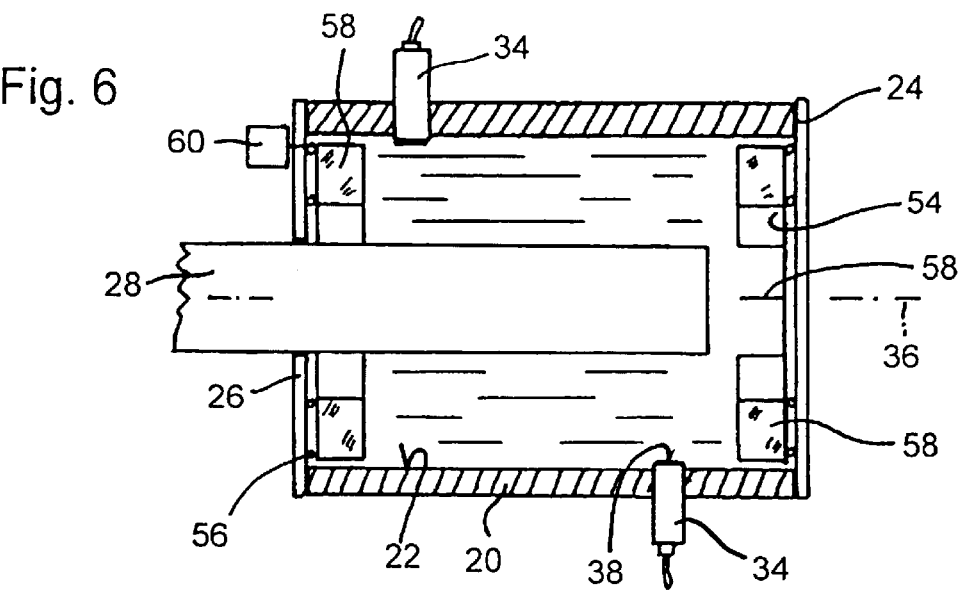
Figure 7:
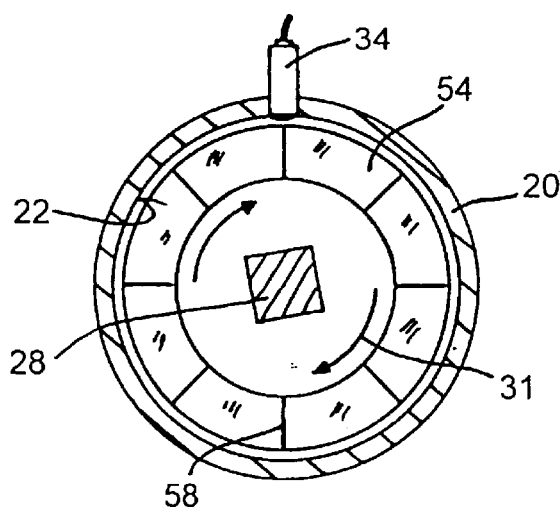
Figure 4:
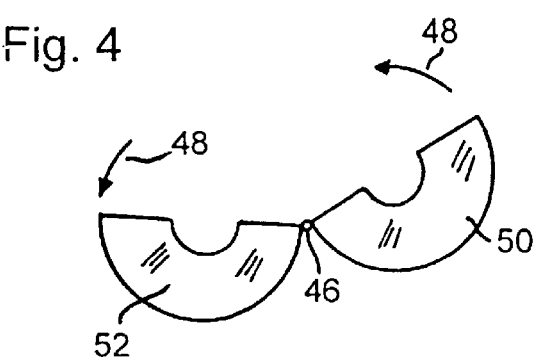
Figure 5:
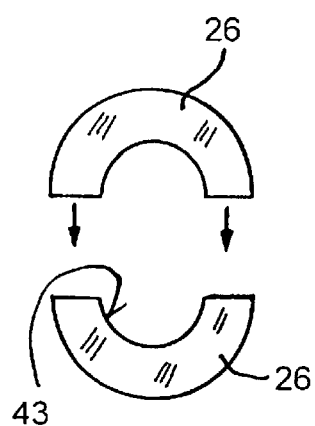

Further advantages and characteristics of the invention will become apparent from the other claims and from the following non restrictive description of embodiments of the invention, given by way of example only with reference to the drawing in which:

FIG. 1: is an axial lengthwise section through a testing device according to the invention with a round bar to be tested, FIG. 2: is a sectional view of the device according to FIG. 1 along the line II—II, FIG. 3: is an axial sectional view showing a testing device with a conical inner lining, FIG. 4: is an axial side view of an openable testing device, FIG. 5: is an axial side view of a guide bush composed of two semi-annular halves that may be assembled, FIG. 6: is another embodiment of a testing device in an illustration according to FIG. 1 with a square bar to be tested and FIG. 7: is a sectional view similar to the illustration according to FIG. 2 for an embodiment similar to that of FIG. 6.

FIG. 1 shows a testing device for the ultrasonic inspection of barstock according to the invention. The device has a tubular tank 20 having a substantially cylindrical interior space 22. It further has two front faces 24 that are each closed by a guide bush 26 being annular in shape so as to leave an opening for the passage of the barstock to be tested.

In the embodiment according to FIG. 1 and FIG. 2 the barstock to be tested is a bar 28 in the form of a round rod that closely fits in sealing means of the two guide bushes 26 and is guided through said guide bushes. It can be transported in the direction of the arrow 30.

A nozzle 32 for the water supply discharges into the interior space 22. As shown in FIG. 2, another nozzle having the same direction is offset by 180 degrees relative thereto. These nozzles 32 are disposed in such a tangential contact with the inner lining that they introduce the water substantially tangentially. A rotating tubular water jacket, as it can be surveyed from FIG. 2, is thus formed. It revolves around the bar 28 to be tested in the direction of the arrows 31.

For the actual ultrasonic testing, three probes 34 are disposed on the tank 20, said three probes being indicated by way of example only and representing the possible probes. A probe emits ultrasound energy on a radial line, another at an angle to the longitudinal axis 36, a third on a radial plane, but not through the center, meaning not through the longitudinal axis 36. Each of the ultrasonic probes 34 has an active face 38 that protrudes into the interior space and is made as flush as possible with the inner lining to the shape of which it conforms. For this purpose, the angle beam probe 34 has a substantially wedged leading member.

The probes as well as the associated, well known test electronics, which has not been discussed in greater detail herein and which corresponds to the state of the art, are devised for the pulse echo technique. Other inspection methods are also possible. The reader is referred in this respect to the book mentioned herein above.

In the exemplary embodiment according to the FIGS. 1 and 2, the water used for coupling exits in the region of the guide bushes 26, more specifically between the guides bushes 26 and the bar 28, and is collected in collecting basins 40 from where it is evacuated.

The radial thickness of the water jacket between bar 28 and inner lining 22 amounts to at least 5 millimeters, it preferably amounts to some centimeters. The flow rate in the direction of rotation is chosen to be such that any kind of bubbles is swept along and that in any case they are not allowed to get trapped somewhere.

The probes 34 can be disposed in a circumferential symmetry on the tank 20. The arrangement depends on the construction of the testing device and can be adapted to the specific inspection requirements.

The tank 20 may be quite short, its axial length needs only be long enough to accommodate all of the probes for the inspection to be carried out.

The mechanical structure of the testing device is quite simple, there are no rotating parts, the only rotating element is the water jacket.

FIG. 3 shows a tank 20 with a slightly conical interior space 22. In this case, the water is introduced through a nozzle 32. It is located in the region with the greater diameter. The water leaves the interior space 22 at an outlet nozzle 42 that is similar in construction and disposed in the same direction. Independent thereof, ridges of a small height ranging for example from 5 to 10 mm are provided that are helically arranged on the inner lining 22 and that serve as guiding plates 44 which are helically arranged on the periphery thereof. They lead the water jacket on a helical path from the inlet to the outlet.

FIG. 4 shows a tank that is divided, in a plane passing through the longitudinal axis 36, into two shells that are joined together by a joint 46 with an articulation axis that is oriented parallel to the longitudinal axis 36 in such a manner that they can be folded together to form a tank according to FIGS. 1 and 2. Corresponding sealing means are provided on the two shells 50, 52. With the appropriate guide bushes 26, said tank 20 can be utilized for inspecting stationary bars, i.e., such bars 28 that are already installed such as tubes in chemical or nuclear plants.

The arrows 48 show how the two shells 50, 52 can be folded together to form a closed tank.

Finally, FIG. 5 shows a guide bush 26 that in the present case is composed of two segments. As a result thereof, the guide bush 26 can be placed onto bars without the ends thereof having to be threaded through or onto stationary, already installed bars in the manner described herein above in connection with the embodiment according to FIG. 4.

To provide a seal against the bars 28, seals 43 are provided on the guide bushes 26, see FIG. 3. The guide bushes 26 can be placed into suited recesses or seats provided on the front faces 24 of the tank 20 in such a manner that they closely fit therein and are readily removable therefrom.

Guide bushes 26 with adjustable openings also proved efficient, e.g., such with an iris diaphragm similar to those known from cameras. With round test samples in particular, it is advantageous to rotate the test sample as it is being conveyed through the testing device. In this way, the local resolution can be improved. A rotating device takes hold of the test sample and rotates it relative to the testing device. The testing device may also be pivoted back and forth, e.g., be rotated 360 degrees back and forth about the longitudinal axis 30. The testing device according to the invention is suited for such applications in which a flaw detected during normal testing or a discrepancy are subsequently examined more closely by moving or rotating the test sample back and forth in such a manner that test sample and/or testing device are moved about the site of the detected flaw in a special test run which permits improved and more specific measurement and detection of the flaw.

In the embodiment according to the FIGS. 6 and 7, the water (or another fluid) inside the cylindrical interior space 22 of the tubular tank 20 is brought to rotate in the direction indicated by the arrows 31 (FIG. 7) by way of two blade wheels 54. The blade wheels 54 are arranged on the front faces and replace these. Bearings 56 for rotatably carrying the blade wheels 54 are provided for this purpose. The blade wheels 54 have a number of individual blades 58 that are substantially located in one diametral plane. There is a lot of space between the various blades 58 so that ultrasound measurement can be carried out between two blades 58 in the case that the blade wheels 54 are not located completely out of the range of movement of the blade wheels 54 as shown in FIG. 6 for example.

The blade wheels 54 are driven by an engine 60 disposed outside. For this purpose, an engine axis extends across the side part and ends in a pinion. The pinion engages in a toothed ring cooperating with the blade wheel 54. Other driving devices for driving the blade wheel 54 are possible. It is also possible to arrange or to mount the blade wheels 45 on the housing 20. The blades 58 shown are connected to an annular disc from which they protrude in the direction counter to the bearing 56. The engine 60 can also be disposed in the housing. As many blades 58 and as many blade wheels 54 as are necessary to form the water jacket wanted are provided for.

FIG. 6 shows the inspection of an end portion of a bar 28 with a substantially square cross section (see FIG. 7). The right front face is closed. It can be provided with a passage for the bar 28, which also applies to the left front face.

It is possible to combine the movement of the water by tangentially introducing the water, see FIGS. 1 and 2, on the one side and driving it by means of a blade wheel 54 on the other side.

What is claimed is:

1. A testing device for the ultrasonic inspection of barstock material having a cross-sectional dimension, the testing device comprising:

a stationary tank defining a substantially cylindrical interior space having a larger inner diameter than the cross-sectional dimension of the barstock material and having an axis;

equipment for producing a water jacket within the interior space and surrounding the barstock material, said equipment being provided with either at least one nozzle for injection of water, wherein said nozzle is disposed in substantially tangential contact with an inner lining of the interior space into which it discharges and/or a blade wheel that is disposed so as to rotate about the axis and that is assigned a rotary drive mechanism; and at least one ultrasonic probe connected to the tank and having an active face wherein the active face is freely accessible from the cylindrical interior space.

2. The testing device according to claim 1, wherein the at least one probe is disposed in such a manner that the active face thereof is made flush with the inner lining of the tank.

3. The testing device according to claim 1, wherein guide means for the barstock material are provided, said guide means being devised for guiding a bar of the barstock material to be tested in such a manner that the bar is substantially concentric with the axis.

4. The testing device according to claim 1, wherein the tank has two front faces and end rings, wherein the end rings can be replaceably fastened to the two front faces of the tank and have an opening that is adapted to the barstock material to be tested.

5. The testing device according to claim 1, wherein the tank has two front faces and a collecting basin is provided beneath at least one front face of the tank, said basin collecting water exiting said front face.

6. The testing device according to claim 1, wherein the tank has an inner lining and an outlet is provided on the tank, which outlet is disposed in substantially tangential contact with the inner lining and in a direction counter to the at least one nozzle for water supply.

7. The testing device according to claim 1, wherein the tank has an inner lining and helically oriented guiding plates are provided on the inner lining.

8. The testing device according to claim 1, wherein the tank has an inner lining and two front faces, the inner lining tapering from one front face toward the other front face.

9. The testing device according to claim 8, wherein the inner lining conically tapers from one front face toward the other front face.

10. The testing device according to claim 1, wherein the active face faces the barstock material.

* * * * *